US008086324B1

(12) United States Patent
Vase

(10) Patent No.: US 8,086,324 B1
(45) Date of Patent: Dec. 27, 2011

(54) INTRAPERICARDIAL LEAD WITH DISTAL REGION CONFIGURED TO OPTIMIZE LEAD EXTRACTION

(75) Inventor: Abhi Vase, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 998 days.

(21) Appl. No.: 11/863,030

(22) Filed: Sep. 27, 2007

(51) Int. Cl.
*A61N 1/372* (2006.01)
*A61N 1/375* (2006.01)

(52) U.S. Cl. ............................ 607/125; 607/38; 607/126

(58) Field of Classification Search .................. 607/38, 607/125, 126
See application file for complete search history.

(56) References Cited

U.S. PATENT DOCUMENTS

| | | | |
|---|---|---|---|
| 4,030,509 A | 6/1977 | Heilman et al. | |
| 4,402,329 A * | 9/1983 | Williams | 607/123 |
| 4,548,203 A | 10/1985 | Tacker, Jr. et al. | |
| 4,821,723 A | 4/1989 | Baker, Jr. et al. | |
| 4,827,932 A | 5/1989 | Ideker et al. | |
| 4,971,070 A | 11/1990 | Holleman et al. | |
| 4,991,583 A | 2/1991 | Silvian | |
| 4,998,975 A | 3/1991 | Cohen et al. | |
| 5,052,407 A | 10/1991 | Hauser et al. | |
| 5,063,932 A | 11/1991 | Dahl et al. | |
| 5,105,826 A | 4/1992 | Smits et al. | |
| 5,191,901 A | 3/1993 | Dahl et al. | |
| 5,300,110 A | 4/1994 | Latterell et al. | |
| 5,314,462 A | 5/1994 | Heil, Jr. et al. | |
| 5,327,909 A | 7/1994 | Kiser et al. | |
| 5,344,439 A | 9/1994 | Otten | |
| 5,385,579 A | 1/1995 | Helland | |
| 5,425,756 A | 6/1995 | Heil, Jr. et al. | |
| 5,476,503 A | 12/1995 | Yang | |
| 5,509,924 A | 4/1996 | Paspa et al. | |
| 5,562,708 A | 10/1996 | Combs et al. | |
| 5,674,251 A | 10/1997 | Combs et al. | |
| 5,837,007 A | 11/1998 | Altman et al. | |
| 5,895,417 A | 4/1999 | Pomeranz et al. | |
| 6,045,565 A * | 4/2000 | Ellis et al. | 606/167 |
| 6,056,744 A | 5/2000 | Edwards | |

(Continued)

FOREIGN PATENT DOCUMENTS

EP 0280564 B1 6/1993

(Continued)

OTHER PUBLICATIONS

European Search Report, Aug. 2, 2007: Related Application Serial No. EP07251557.

*Primary Examiner* — Carl H Layno
*Assistant Examiner* — Natasha Patel

(57) ABSTRACT

A lead includes a lead body with a stylet receiving lumen, a distal tip, and a distal portion proximal of the distal tip that is biased to assume a non-linear configuration. Insertion of a stylet into the lumen causes the distal portion to transition from the non-linear configuration to a generally linear configuration. The lead also includes a first arm member having a distal end and a proximal end coupled to the lead body proximal of the distal tip; and a nosepiece, at least a portion of which is biodegradable. The nosepiece is configured to receive the distal tip of the lead body and the distal end of the first arm member such that the lead body, first arm member and nosepiece form a closed arrangement prior to biodegradation of the nosepiece and an open arrangement after biodegradation of the nosepiece.

22 Claims, 14 Drawing Sheets

U.S. PATENT DOCUMENTS

| | | | |
|---|---|---|---|
| 6,141,594 A * | 10/2000 | Flynn et al. | 607/127 |
| 6,253,106 B1 | 6/2001 | Legay et al. | |
| 6,330,481 B1 | 12/2001 | Van Wijk et al. | |
| 6,463,335 B1 | 10/2002 | Munch et al. | |
| 6,473,645 B1 | 10/2002 | Levine | |
| 6,741,878 B2 | 5/2004 | Fuimaono et al. | |
| 6,941,174 B2 | 9/2005 | Shchervinsky | |
| 6,966,322 B2 | 11/2005 | McVenes et al. | |
| 2002/0151948 A1 | 10/2002 | King et al. | |
| 2003/0028224 A1 | 2/2003 | McVenes et al. | |
| 2003/0212446 A1 | 11/2003 | Kaplan et al. | |
| 2004/0015193 A1 | 1/2004 | Lamson et al. | |
| 2004/0054391 A1 | 3/2004 | Wildon | |
| 2004/0059404 A1 | 3/2004 | Bjorklund et al. | |
| 2004/0087831 A1 | 5/2004 | Michels et al. | |
| 2004/0267303 A1 | 12/2004 | Guenst | |
| 2005/0090870 A1 | 4/2005 | Hine et al. | |
| 2005/0102003 A1 | 5/2005 | Grabek et al. | |
| 2005/0113900 A1 | 5/2005 | Shiroff et al. | |
| 2005/0119718 A1 | 6/2005 | Coe et al. | |
| 2005/0131511 A1 | 6/2005 | Westlund | |
| 2005/0137672 A1 | 6/2005 | Coe et al. | |
| 2005/0137674 A1 | 6/2005 | Coe et al. | |
| 2005/0149138 A1 | 7/2005 | Min et al. | |
| 2006/0020317 A1 | 1/2006 | Flach et al. | |
| 2007/0293922 A1 * | 12/2007 | Soltis et al. | 607/122 |

FOREIGN PATENT DOCUMENTS

| | | |
|---|---|---|
| EP | 0571985 B1 | 12/1999 |
| EP | 0589633 B1 | 1/2000 |
| WO | 02085425 A1 | 10/2002 |
| WO | 2005039691 A1 | 5/2005 |

* cited by examiner

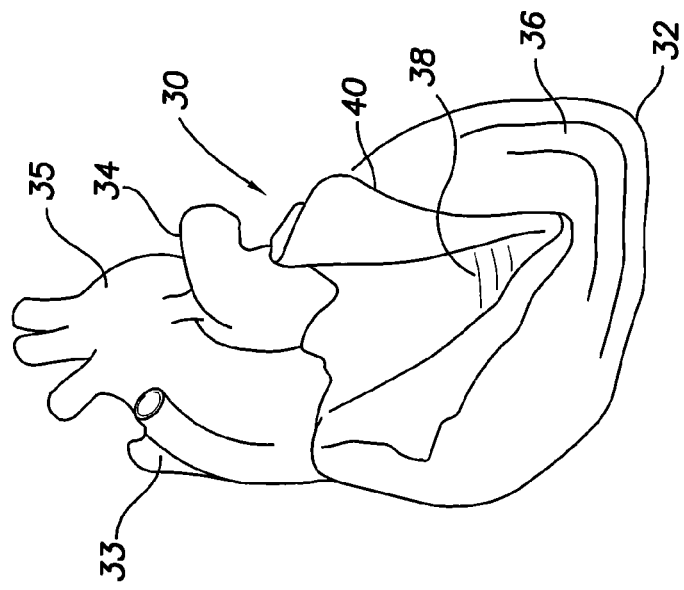
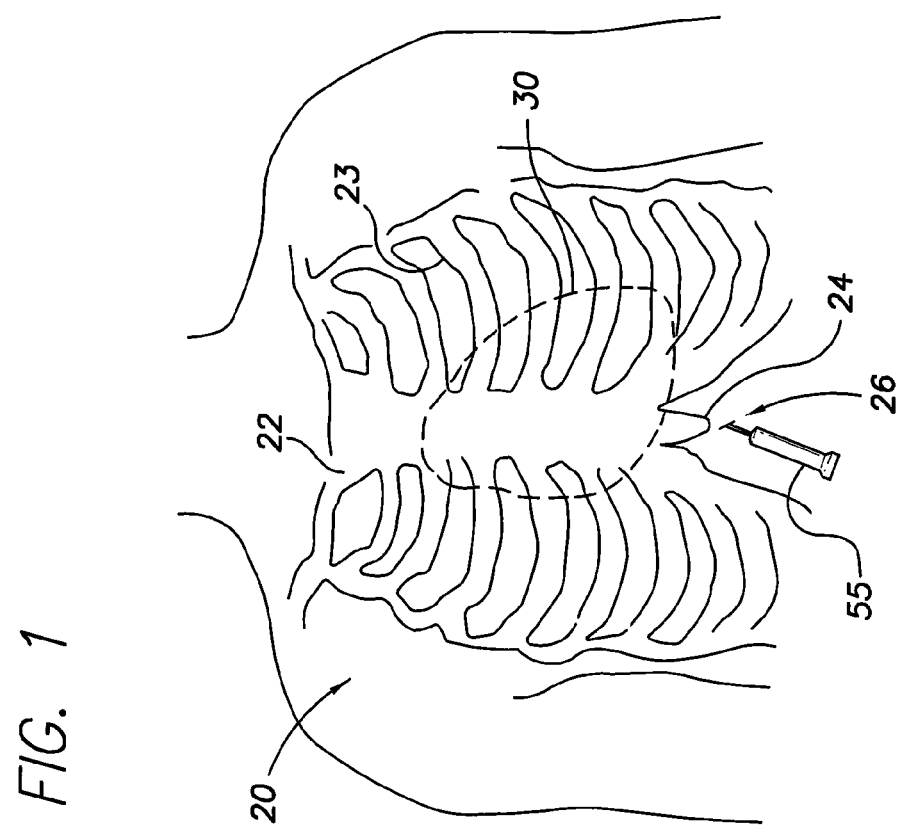
FIG. 1
FIG. 2

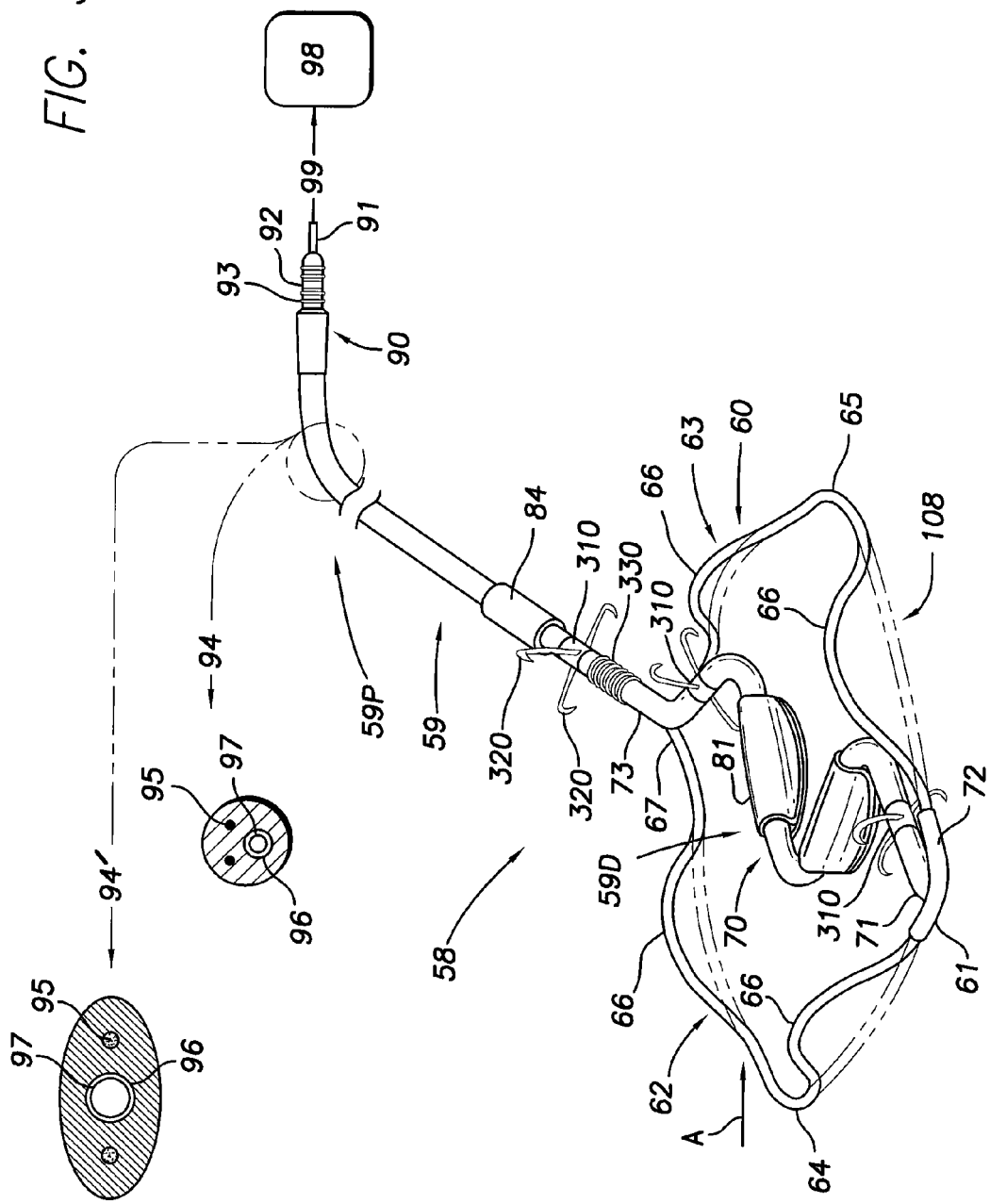

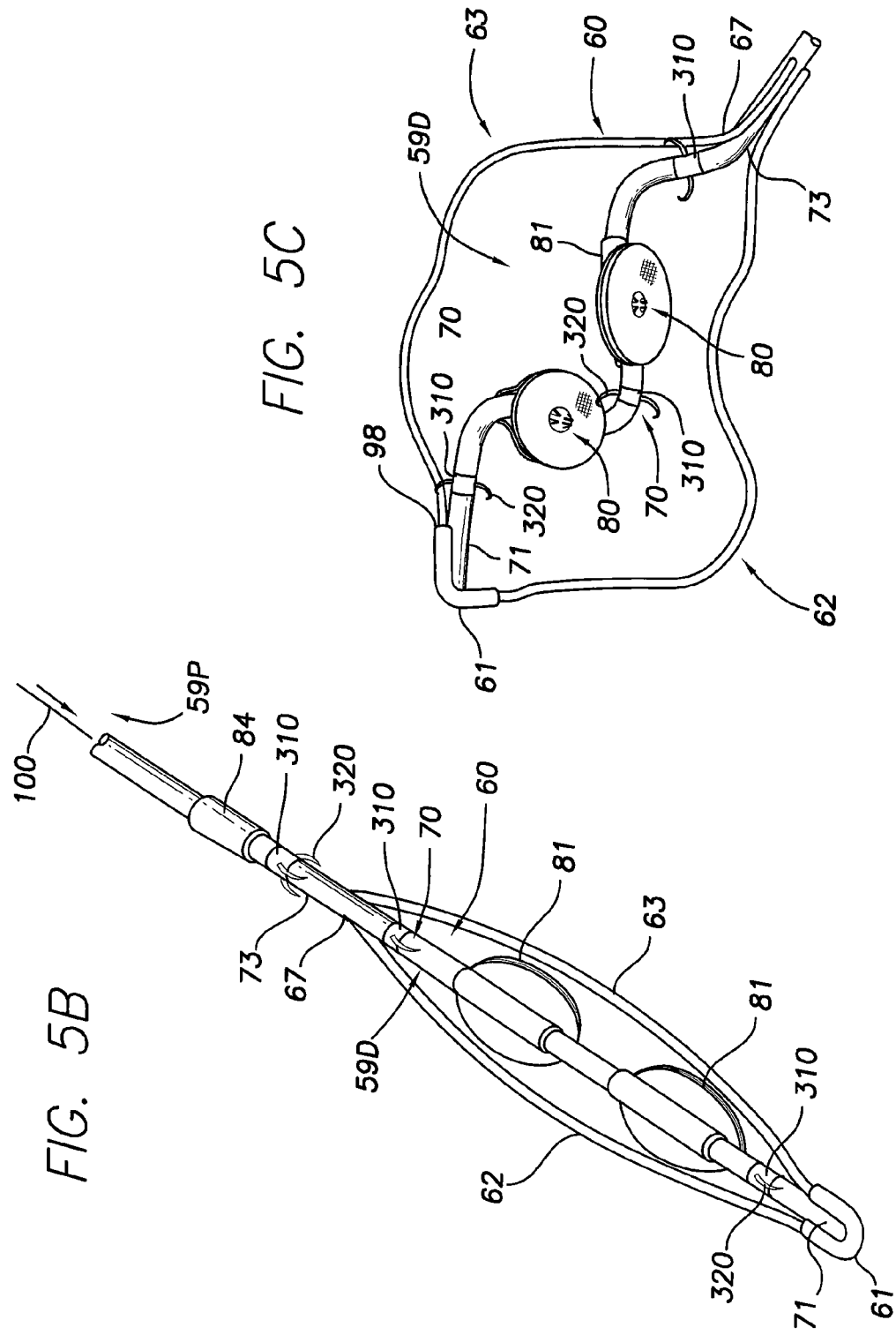

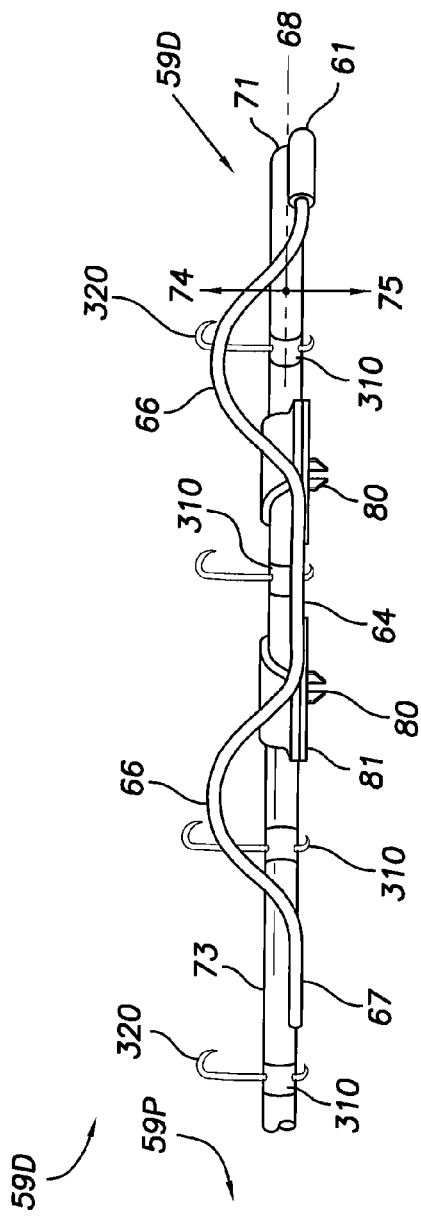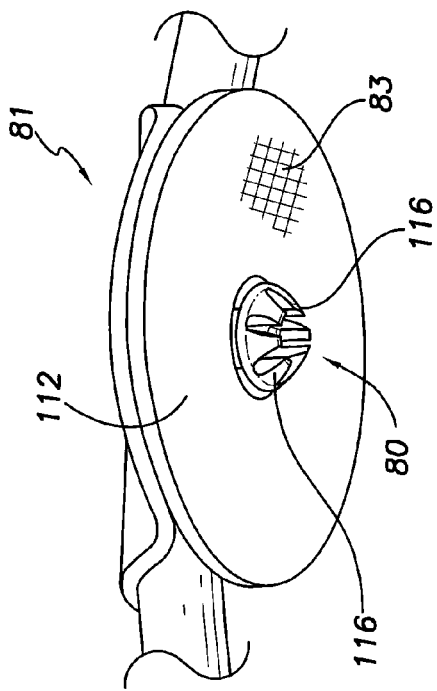
FIG. 5D
FIG. 5E

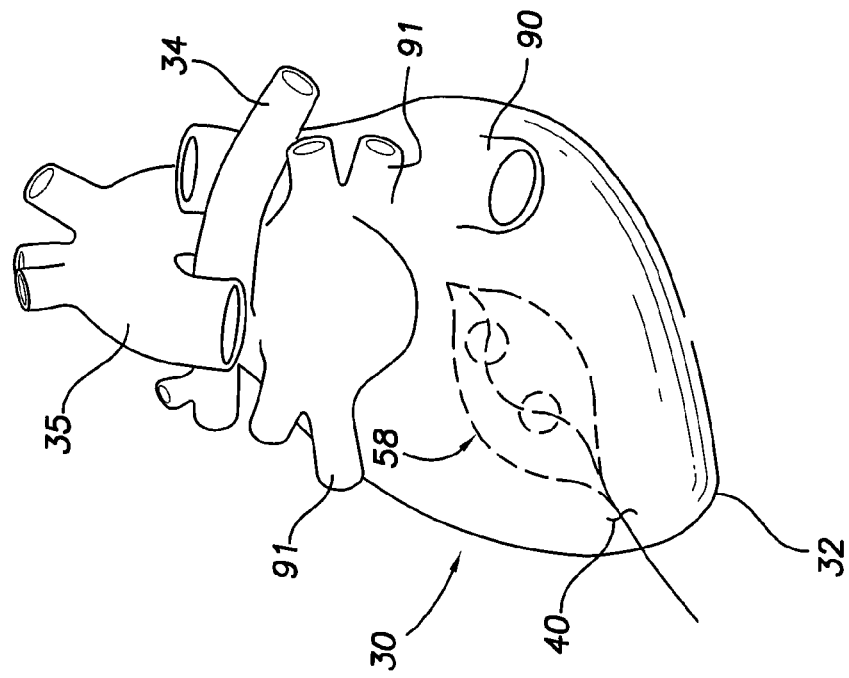
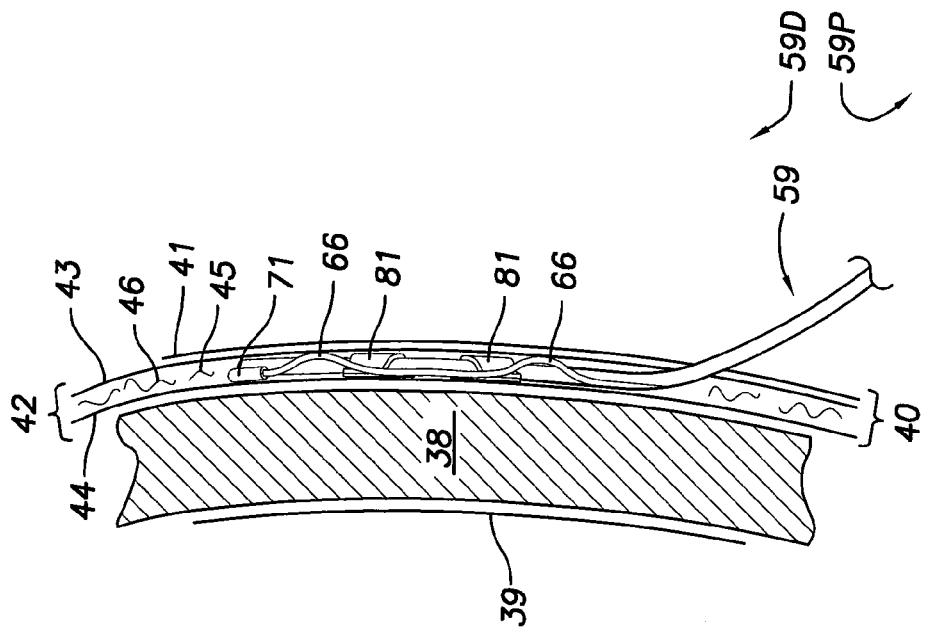
FIG. 7
FIG. 6

INTRAPERICARDIAL LEAD WITH DISTAL REGION CONFIGURED TO OPTIMIZE LEAD EXTRACTION

CROSS REFERENCE TO RELATED APPLICATIONS

The application is related to U.S. patent application Ser. No. 11/691,335, filed Mar. 26, 2007, titled "Intrapericardial Lead", now U.S. Pat. No. 7,899,555; and U.S. patent application Ser. No. 11/833,511, filed Aug. 3, 2007, titled "Intrapericardial Lead with Distal Portion Configured to Promote Lead Fixation."

FIELD OF THE INVENTION

The present invention relates generally to implantable cardiac electrotherapy leads carrying electrodes for electrically stimulating body tissue and/or for sensing the electrical activity of such tissue. More particularly, the invention relates to implantable cardiac electrotherapy leads configured for secure placement within the intrapericardial space of the human heart.

BACKGROUND OF THE INVENTION

Implantable cardiac electrotherapy leads are electrically coupled to implantable cardiac electrotherapy devices such as pacemakers, defibrillators or implantable cardioverter defibrillators ("ICD"). Leads connecting such devices with the heart may be used for pacing or for sensing electrical signals produced by the heart or for both pacing and sensing in which case a single lead serves as a bi-directional pulse transmission link between the device and the heart. The lead typically includes a distal end portion for carrying a tip electrode and a ring electrode. The lead may also carry one or more cardioverting and/or defibrillating electrodes proximal of the ring electrode.

Various lead types for different placement approaches have been developed. For example, an endocardial type lead is one that is inserted into a vein and guided therethrough to a target location, for example, in one or both of the chambers of the right side of the heart or within one of the veins of the coronary sinus region of the heart for left side stimulation and/or sensing. The distal end portion of an endocardial lead may carry a helical, screw-in tip element, electrically active or inactive, and/or outwardly projecting tines or nubs and/or a sinuous shape for anchoring the lead.

There are factors, however, which warrant alternatives to a transvenous lead implant approach. These factors include coronary sinus and/or coronary venous obstructions. Furthermore, the coronary veins dictate the implant location of the electrode, which can make optimal left side lead placement impossible and may cause long and unpredictable implant times. In addition, approximately 10% of the patient population is unable to receive this type of lead due to vasculature anomalies. In such cases, epicardial or myocardial type leads may be used. Such leads are attached directly to the epicardium using sutures or another fixation mechanism such as a helical screw-in electrode that engages the myocardium. Myocardial leads typically are used for temporary pacing or for permanent pacing following open-heart surgery.

Conventional approaches to the placement of epicardial leads usually involve thoracotomies or sternotomies. Such placement techniques have disadvantages including the relatively large incisions needed to gain access to the thoracic cavity and to the heart; the difficulty of quickly and easily attaching the lead; the high rate of patient morbidity, trauma and pain; the tendency to require longer in-patient recovery times; and the unattractiveness of the scars left by the procedure.

To mitigate these disadvantages, minimally invasive lead placement techniques have been developed for placing a myocardial lead on the surface of the heart via a small, finger size opening in the chest. Such techniques may include the use of a fiber optics video camera of the type commonly used in other thoracic surgeries (for example, lung biopsies and other thoracic cavity and cardiac procedures) for visually imaging, and thereby aiding, the lead placement procedure. These minimally-invasive lead placement techniques allow for faster, safer and easier myocardial lead placements with significantly less morbidity, trauma and pain to the patient.

It is not unheard of for an implanted lead to require extraction due to shifting of the lead, lead failure, improper implantation, changes in the electrical characteristics of the implantation site, etc. As with all types of implantable leads, including leads implanted via minimally-invasive techniques, extraction of an implanted lead can be risky for the patient and difficult due to the configuration of the lead and/or tissue ingrowth about the lead.

There is a need in the art for a lead that facilitates the accurate placement and subsequent anchoring thereof within the intrapericardial space while providing for a reduced level of difficulty and risk during potential future extraction of the lead. There is also a need in the art for method of intrapericardially implanting and extracting such a lead.

SUMMARY

Disclosed herein is an intrapericardial lead configured for improved extraction. In one embodiment, the lead includes a lead body including a stylet receiving lumen, a distal tip, and a distal portion proximal of the distal tip and biased to assume a non-linear configuration, wherein insertion of the stylet into the lumen such that the distal tip is distally displaced relative to the rest of the lead body causes the distal portion to transition from the non-linear configuration to a generally linear configuration. The lead also includes a first arm member having a distal end, and a proximal end coupled to the lead body proximal of the distal tip; and a nosepiece, at least a portion of which is biodegradable, configured to receive the distal tip of the lead body and the distal end of the first arm member such that the lead body, first arm member and nosepiece form a closed arrangement prior to biodegradation of the nosepiece and an open arrangement after biodegradation of the nosepiece.

Also disclosed herein is an intrapericardial lead configured for improved fixation and extraction. In one embodiment, the lead includes a lead body including a stylet receiving lumen, a distal tip, and a distal portion proximal of the distal tip and biased to assume a non-linear configuration, wherein insertion of the stylet into the lumen such that the distal tip is distally displaced relative to the rest of the lead body causes the distal portion to transition from the non-linear configuration to a generally linear configuration. The lead also includes a first arm member having a distal end coupled to the distal tip and a proximal end coupled to the lead body proximal of the distal tip; and a fixation member mounted on the lead body and including a biodegradable portion.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a front view of a human rib cage showing a heart within the cage.

FIG. 2 is an enlarged view of the heart of FIG. 1 with the pericardium partially opened to reveal the myocardium within.

FIG. 5A is a top perspective view of a cardiac lead in a deployed or expanded state.

FIG. 5B is a top perspective view of the cardiac lead depicted in FIG. 5A, wherein a distal portion of the lead is urged into a configuration suitable for insertion through a lumen.

FIG. 5C is a bottom perspective view of the lead embodiment depicted in FIG. 5A.

FIG. 5D is a side view of the lead embodiment depicted in FIG. 5A, as viewed from the direction of arrow A in FIG. 5A.

FIG. 5E is an enlarged view of electrode structure in FIG. 5C.

FIG. 6 is a view similar to FIG. 3 and shows the cardiac lead of FIG. 5A inserted into a pericardial space.

FIG. 7 is a posterior view of the heart of FIG. 2 with the lead embodiment of FIGS. 5A-5E inserted as shown in FIG. 6.

DETAILED DESCRIPTION

Figure 4:
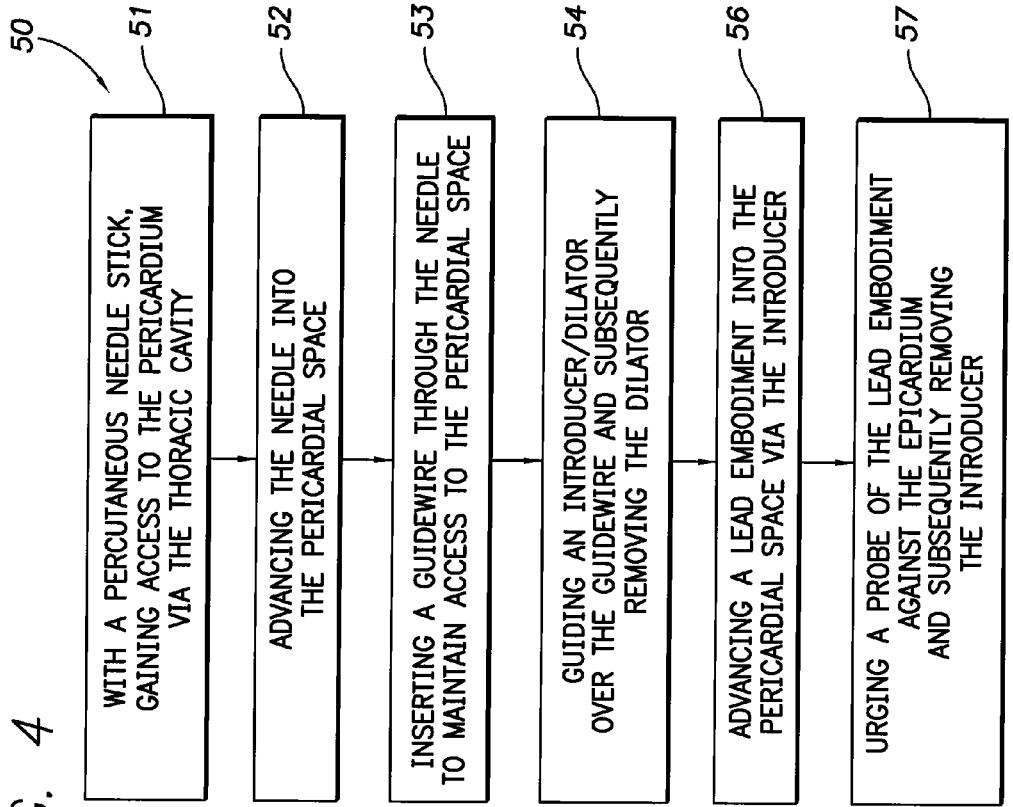
FIG. 4 is a flow chart that describes an intrapericardial implant procedure for a cardiac lead.

Disclosed herein are various embodiments of implantable cardiac electrotherapy leads that facilitate and enhance the accurate placement (and monitoring of that placement) of medical electrodes. Although the lead embodiments may be used in a variety of medical procedures, they are especially suited for installation as a cardiac lead into the pericardial space of the heart. This installation may be made, for example, via percutaneous subxiphoid procedures. In order to best understand the novel structure of these embodiments, their placement, and their subsequent use, a description of the structure is preceded by the following review of heart and chest structures.

FIGS. 1 and 2 respectively illustrate the chest and heart structures and, in particular, the reference numeral 20 in FIG. 1 schematically illustrates the human chest and shows the sternum 22 and the ribs 23 which attach to the sternum. The ribs and the sternum form a "rib cage" which provides a protective covering around the heart, lungs and other vital organs. Positioned at the lower end of the sternum 22, is a small piece 24 of cartilage known as the xiphoid process or cartilage. The region 26 immediately below the xiphoid process is commonly referred to as the subxiphoid region. Finally, lying within the rib cage is the heart 30 (shown in broken lines).

An enlarged view of the heart 30 is shown in FIG. 2. The body of the heart extends upward from an apex 32 to where it joins with various vein and artery structures that make up the heart's blood vessels. For example, the superior vena cava 33 is one of the major vessels that pass oxygen-depleted blood from the body into the right atrium of the heart. A pair of pulmonary arteries 34 (only one shown) route blood from the right ventricle to the lungs. After oxygen-rich blood is returned from the lungs to the left atrium, the left ventricle pumps it out to the body through the aortic arch 35.

Surrounding the body of the heart 30 is the pericardium 40, which is a double walled sac of fibrous tissue that surrounds the heart up to the roots of the heart's blood vessels. In FIG. 2, the pericardium has been cut and folded back to reveal the myocardium 38, which is the muscular tissue that principally forms the walls of the heart. The myocardium 38 is again shown in FIG. 3, which is an enlarged section through the heart wall. A membrane known as the endocardium 39 forms an inner lining of the myocardium and, as shown, the pericardium 40 overlies the myocardium.

An outer portion of the pericardium is the fibrous pericardium 41, which is formed of dense connective tissue to protect the heart and anchor it to chest structures (e.g., the diaphragm and the back of the sternum). The inner portion of the pericardium is the serous pericardium 42, which has two layers. The outer layer is the parietal pericardium 43, which lies next to the fibrous pericardium 41. The inner layer is the visceral pericardium, which is typically called the epicardium 44.

The fibrous pericardium 41 and parietal pericardium 43 are collectively referred to as the "pericardial sac." The parietal 43 and visceral 44 layers are spaced apart to form the pericardial space 45, which is filled with serous fluid generally called the pericardial fluid 46. The pericardial fluid acts to reduce surface tension and facilitate free movement of the myocardium. The term epicardial is typically used to refer to the outside surface of the heart.

Cardiac lead embodiments disclosed herein are configured for insertion along an insertion path 49 through the pericardial sac and into the pericardial space 45 to facilitate secure attachment to the epicardium 44. Before directing attention to the lead embodiments, a method for placing a cardiac lead of the lead embodiments disclosed herein will be described with reference to the flow chart 50 of FIG. 4. In a first process step 51, a percutaneous needle stick is used to gain access to the pericardium 40 via the thoracic cavity. One embodiment of this process applies the needle stick to the subxiphoid region 26 of FIG. 1.

Figure 3:
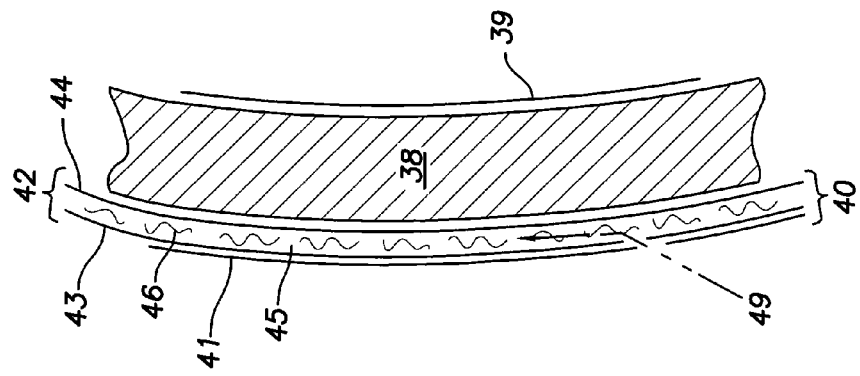
FIG. 3 is an enlarged view of a section of the wall of the heart of FIG. 2.

In a second process step 52, the needle is advanced along the path 49 (FIG. 3) of FIG. 3, through the pericardial sac and into the pericardial space 45. In step 53 a guidewire is inserted through the needle to maintain access to the pericardial space, after which, the needle is removed, leaving the guidewire in the pericardial space. In step 54 an introducer/dilator is placed over the guidewire to facilitate introduction of a cardiac lead. Subsequently, the dilator is removed leaving an introducer (55 in FIG. 1) inserted into the xiphoid region 26 and pericardial space. In step 56, the lead is advanced through the introducer 55 and into the pericardial space (45 in FIG. 3). Finally, in step 57 the distal end of the lead is urged against the epicardium (44 in FIG. 3). The introducer is then removed. Because a variety of guidewires, dilators and introducers are known in the art, their details have been omitted. One possible introducer for use in placing an intrapericardial lead is described in U.S. patent application Ser. No. 11/609,751, titled Intrapericardial Delivery Tools and Methods, the disclosure of which is hereby incorporated by reference.

For a discussion regarding the exemplary lead embodiment disclosed herein, reference is made to FIGS. 5A-5E. As shown in these figures, a cardiac lead embodiment 58 includes a lead body 59, which extends from a proximal portion 59P to a precurved distal end portion 59D. The proximal portion terminates in an electrical connector assembly 90 described below.

The precurved distal end portion 59D of the lead body has an atraumatic tip 71. In one embodiment, the tip 71 is closed and of sufficient strength to arrest the distal progression of a stylet through a central lumen 96 of the lead body, wherein the lumen may be lined with a helically wound conductor coil 97 extending through the lumen. Thus, as will discussed later in this Detailed Description, when the stylet is distally displaced within the lumen 96, the distal end of the stylet abuts against the tip 71 and causes the lead body to extend and straighten, as shown in FIG. 5B. In one embodiment, the tip 71 is strengthened via an internal reinforcement such as a metal cap or ring imbedded in the tip and coaxial with the axis of the lumen 96.

In one embodiment, the tip 71 is open such that a portion of the lumen 96 daylights at the tip. In such an embodiment, the tip 71 is configured such that the stylet distal end will not pass through the tip end of the lumen. For example, in one embodiment, the lumen 96 necks down near the tip to prevent the stylet from exiting the lumen, thereby allowing the stylet to straighten the lead body as described above with respect to a closed tip 71.

As depicted in the cross-sections 94, 94' taken through the lead body in FIG. 5A, in various embodiments, the lead body 59 has a circular cross section as illustrated at 94. In other embodiments, the lead body 59 has an oval cross section as depicted at 94'. The circular or oval cross sections may be employed with any of the lead body embodiments disclosed herein. Regardless of the cross sectional configuration of a lead body, the lead body 59 preferably is a multilumen structure of silicone rubber, polyurethane or similar biocompatible, biostable material. In the examples shown, the lead body defines two lumens 95 for receiving electrical conductors and a third lumen 96 for receiving a stylet. The lumen 96 may be lined with a helically wound conductor coil 97, which assists in preventing the stylet from piercing through the wall of the lumen 96.

The precurved distal end portion 59D of the lead body has a preferably closed distal tip 71 and carries a precurved loop member 60, which has a distal segment 61 and is preferably formed of a resilient metal so the loop member 60 will recover to a relaxed loop configuration (FIGS. 5A and 5C) upon being released from an extended, elongated configuration 60E (shown in FIG. 5B). The closed distal tip 71 is compatible with the use of a stylet to drive the distal end portion 59D of the lead body and the loop member 60 carried thereby to a target location within the pericardial space 45. It will be apparent, however, to those skilled in the art that the distal tip 71 may have an aperture in communication with a longitudinally-extending lumen within the lead body 59 to permit delivery of the lead to its destination by means of a guide wire in accordance with well-known "over-the-wire" lead placement techniques. In one embodiment, the distal end 71 of the lead body 59 is joined to the distal segment 61 by, for example, a medical-grade adhesive 72, and the distal end portion 70 is preformed into a normally sinuous configuration 70S.

As illustrated in FIGS. 5A and 5C, in one embodiment, the loop 60 defines first and second wings or loop portions 62, 63, which are positioned on opposite sides of the distal end portion 70. The loop portions 62, 63 respectively extend outward to first and second tips 64, 65, which are farthest spaced from the distal end portion 70.

As shown in FIG. 5D, in one embodiment, the distal segment 61 and the tips 64 and 65 (not visible) substantially lie in a common plane 68 and at least one of the wings defines a hump 66 that is spaced from the corresponding wing tip. In another embodiment, each of the first and second loop portions 62, 63 defines a pair of humps 66 that curve upwardly (as seen in FIG. 5D) away from the common plane 68. FIG. 5D indicates first and second sides 74 and 75 of the common plane 68 and in the example shown, the humps 66 are shown to extend towards the first side 74.

With reference to FIG. 5B, although a pair of loop portions 62, 63 disposed symmetrically about a longitudinal center line 100 of the lead body is preferred, it will become evident from the ensuing description that other arrangements may be feasible, including, without limitation, an asymmetrical arrangement comprising a single loop portion, the provision of a pair of bilaterally disposed loop portions offset in the longitudinal direction to provide a smaller frontal area to facilitate delivery, or multiple loop portions on one or both sides of the longitudinal center line 100. In addition, in another alternative embodiment, some or all of the humps 66 may be formed to curve downwardly relative to the plane 68.

As stated above, the distal end portion 70 of the lead body assumes normally a sinuous configuration when it is not urged into its linear configuration. The sinuous configuration extends from the distal closed end 71 to a proximal end 73 of the sinuous configuration and can take on various curved, serpentine forms in different lead embodiments.

In a manner similar to the distal end portion 70 of the lead body, the loop member 60 assumes the normally expanded state as shown in FIG. 5A. The loop configuration 60 is arranged between its distal segment 61 and a proximal segment 67, which is coupled to the distal end portion 70 in the region of the proximal end 73. The loop member 60, in plan view, may take various forms. For example, the embodiment of FIG. 5A has a generally diamond-shaped configuration. Other configurations, such as square, rectangle, circular, elliptical, and so forth, may be utilized.

As indicated in FIG. 5A, in some embodiments, the lead will have two electrodes 305. However, in other embodiments, a lead will have a single electrode 305 or three or more electrodes 305.

As shown in FIGS. 5A-5E, the distal end portion 70 of the lead body carries at least one, and preferably a plurality of passively fixed or anchored electrode assemblies 81 within the confines of the loop member 60. Each electrode assembly 81 may comprise a shield 112 of, for example, silicone rubber, secured to the distal end portion 70 and surrounding an electrode 80. In the lead embodiment shown, each electrode 80 carries a plurality of prongs 116 that protrude from a flat surface of the corresponding shield 81. The prongs 116 serve to grip the pericardial tissue and to concentrate the electrical current density. The electrodes 80 are preferably formed from a biocompatible and biostable electrically conductive metal (e.g., gold, platinum, or titanium) or metal alloy (e.g., platinum/iridium or stainless steel). The electrode assemblies 81 are arranged on the distal end portion 70 so that the electrodes 80 and prongs 116 are directed towards the second side 75 of the common plane 68 of FIG. 5D.

Preferably, the surface of the shield 112 that surrounds the electrode 80 is covered with a polymer fixation mesh 83. After the distal end portion 59D has been implanted in the pericardial space (45 in FIG. 3), epicardium tissue grows into the mesh 83 and further fixes the electrode assemblies 81 in place. To further stabilize the lead body within the pericardial space, a mesh sleeve 84 may be provided about the lead body proximal of the distal end portion. After pericardial tissue has also grown into this mesh sleeve 84, the lead is further fixed within the pericardial space. To ameliorate inflammatory responses, each of the electrodes 80 may include a bore (not shown) for housing a drug dispensing member such as an absorbent drug-eluting plug loaded with a steroid solution or the like.

Figure 8:
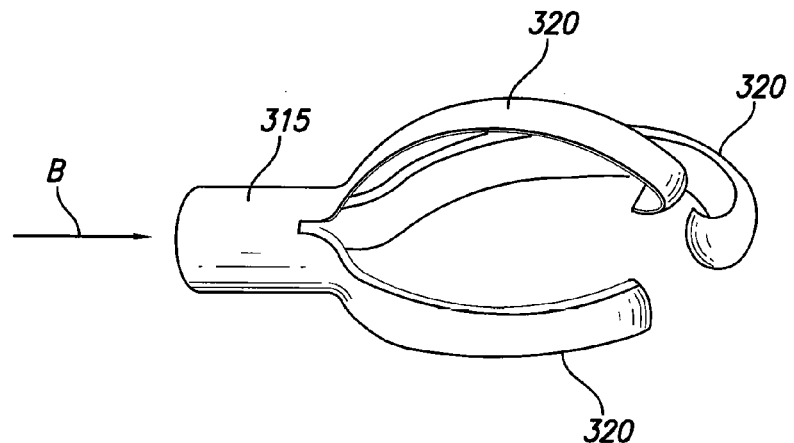
FIG. 8 is a perspective view of a self-expanding fixation member that mounts on the lead tubular body.
Figure 9:
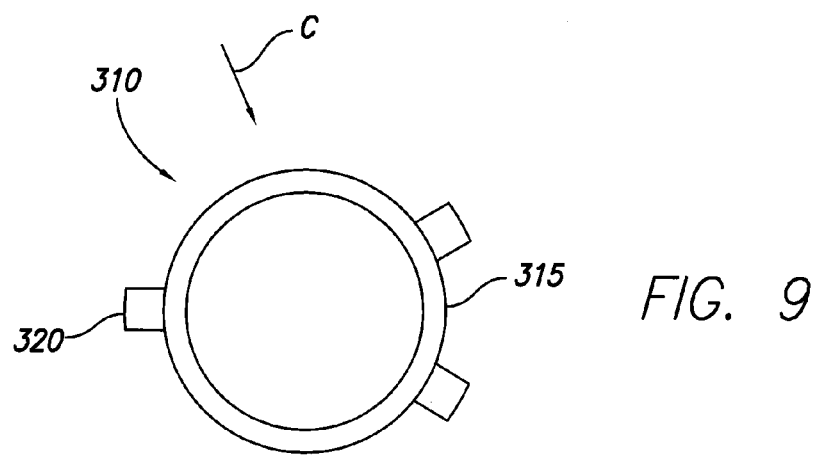
FIG. 9 is an end view of the self-expanding fixation member as viewed from the direction of arrow B in FIG. 8.
Figure 10:
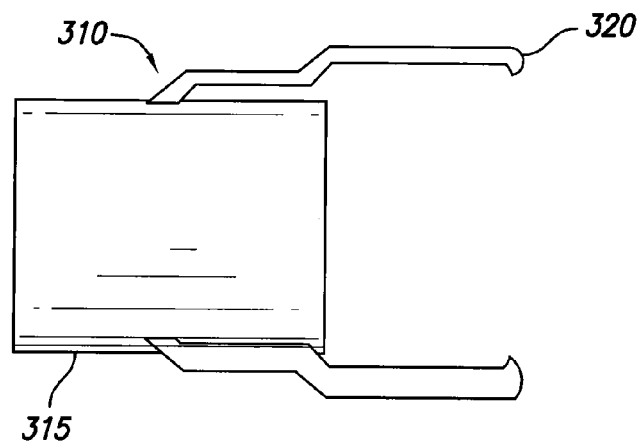
FIG. 10 is a side view of the self-expanding fixation member as viewed from the direction of arrow C in FIG. 9.

As depicted in FIGS. 5A-5D, in one embodiment, one or more fixation members 310 will be located on the lead body at different locations. In other embodiments, the lead will not include such fixation members 310. As indicated in FIGS. 8-10, in one embodiment, the fixation members 310 will include a sleeve 315 or other feature for receiving therein the lead body 59 or otherwise attaching fixation members 310 to the lead body. In one embodiment, the fixation members 310 will include tines, flanges or fingers 320 that extend away from the sleeve 315 and the lead body when not constrained against the lead body by an introducer sheath (55 in FIG. 1) used to insert the lead distal end 70 into the pericardial space (45 in FIG. 6).

Figure 11:
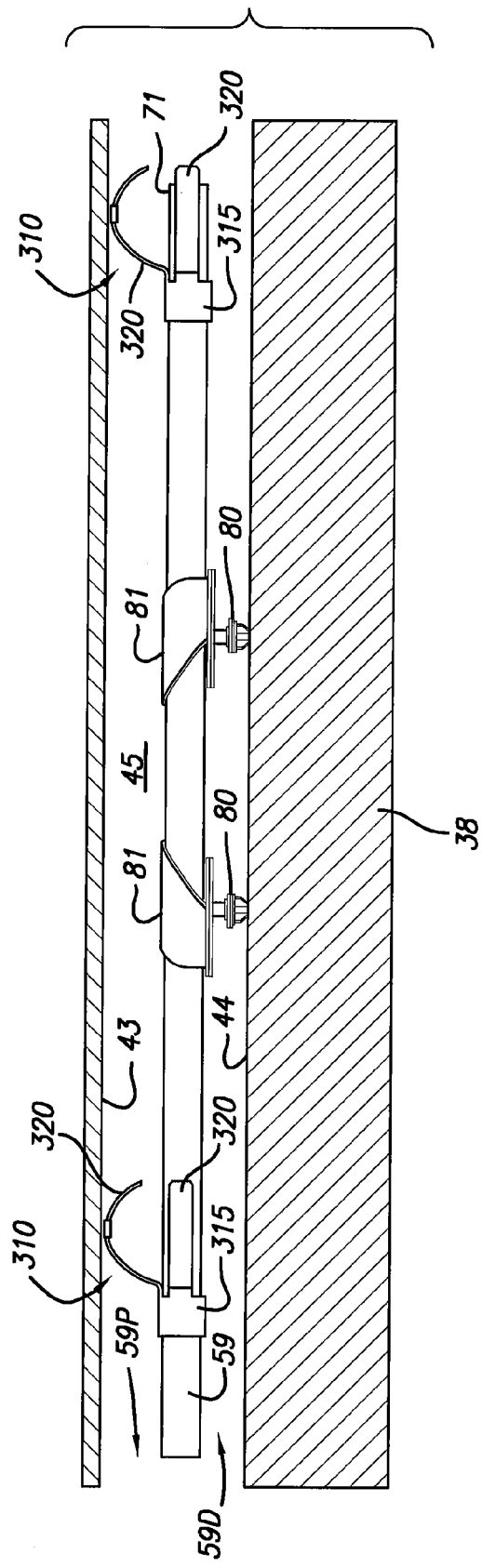
FIG. 11 is a view similar to FIG. 6, except further enlarged and depicting the cardiac lead of FIG. 5A inserted in the pericardial space, the self-expanding fixation members engaging the parietal pericardium and the loop being hidden for clarity purposes.

As illustrated in FIGS. 5A and 5D and best understood from FIG. 11, the fingers 320 project distally from the sleeve 315. Thus, when the introducer sheath (55 in FIG. 1) is proximally withdrawn from about the lead distal end 70 implanted in the pericardial space 45, the fingers 320, which are no longer constrained against the lead body 59, bias outwardly from the lead body to encounter the parietal layer 43 and force the electrodes 80 into contact with the epicardium 44, thereby providing good fixation and stability for the lead. Because the fingers 320 point distally, an introducer sleeve can be distally slid over the proximal side of the fingers 320 to force the fingers back against the lead body 59, thereby allowing the lead distal end 59D to be repositioned at or removed from the lead implantation site in the pericardial space 45.

Depending on the embodiment of the fixation member 310, it has been found that the dimensional configuration of a fixation member 310 can determine whether the fixation member 310 will provide adequate fixation, inadequate fixation, or result in tearing of the pericardial sac. For example, if the tines or fingers 320 do not extend sufficiently from the lead body 59, the fixation will be inadequate, and if the tines 320 excessively extend the result can be tearing of the pericardial sac.

Figure 16:
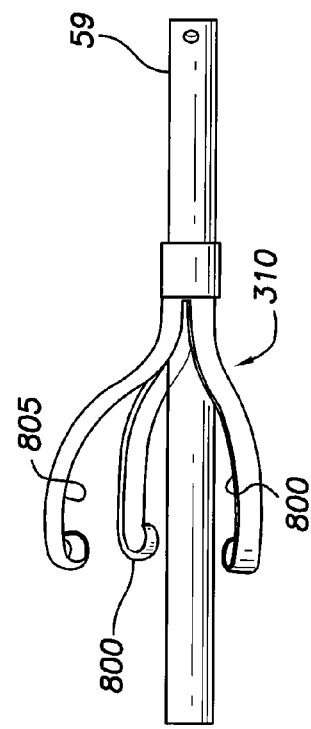
FIG. 16 is an isometric view of a fixation member.
Figure 17:
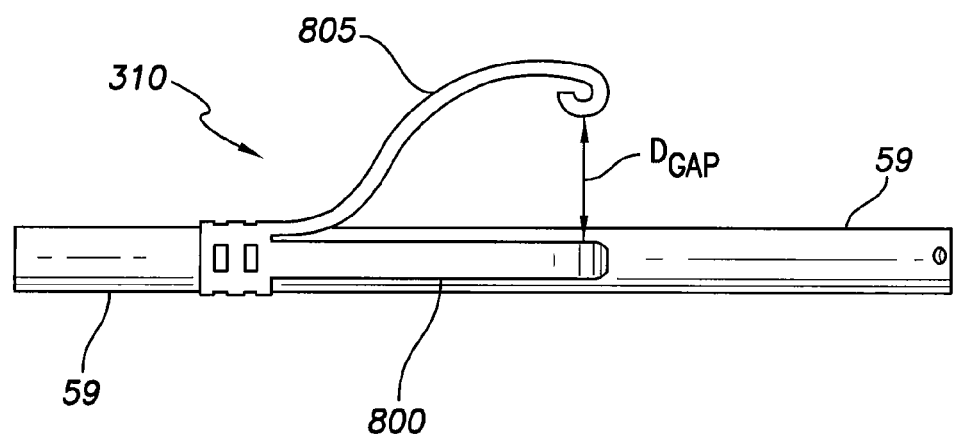
FIG. 17 is a side view of the fixation member depicted in FIG. 16.
Figure 18:
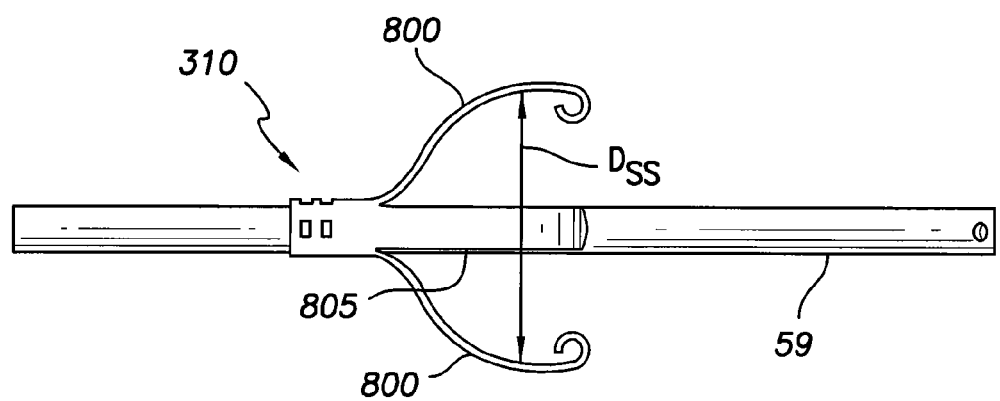
FIG. 18 is a top view of the fixation member depicted in FIG. 16.

One embodiment of a particularly advantageous fixation member 310, which offers the right combination of fixation without tearing of the pericardial sac, is depicted in FIGS. 16-20. As indicated in FIGS. 16-18 and as can be understood from FIGS. 5A and 5D, in one embodiment, the fixation member 310 includes a two smaller lateral or side tines 800 and a single larger top tine 805. As indicated in FIGS. 17 and 18, in one embodiment, when the tines 800, 805 of the fixation member 310 are fully expanded, the distance $D_{ss}$ between the side tines 800 is approximately 0.366 inch, and the gap distance $D_{GAP}$ between the side of the lead body 59 and the tip of the top tine 805 is approximately 0.12 inch. In a similar manner, the gap distance $D_{GAP}$ between the side of the lead body 59 and the tip of a side tine 800 is approximately 0.107 inch. When the tines 800, 805 are collapsed against the lead body 59, the fixation member 310 and collapsed tines 800, 805 have a diameter of approximately 0.152 inch is approximately 11.5 French.

Figure 19:
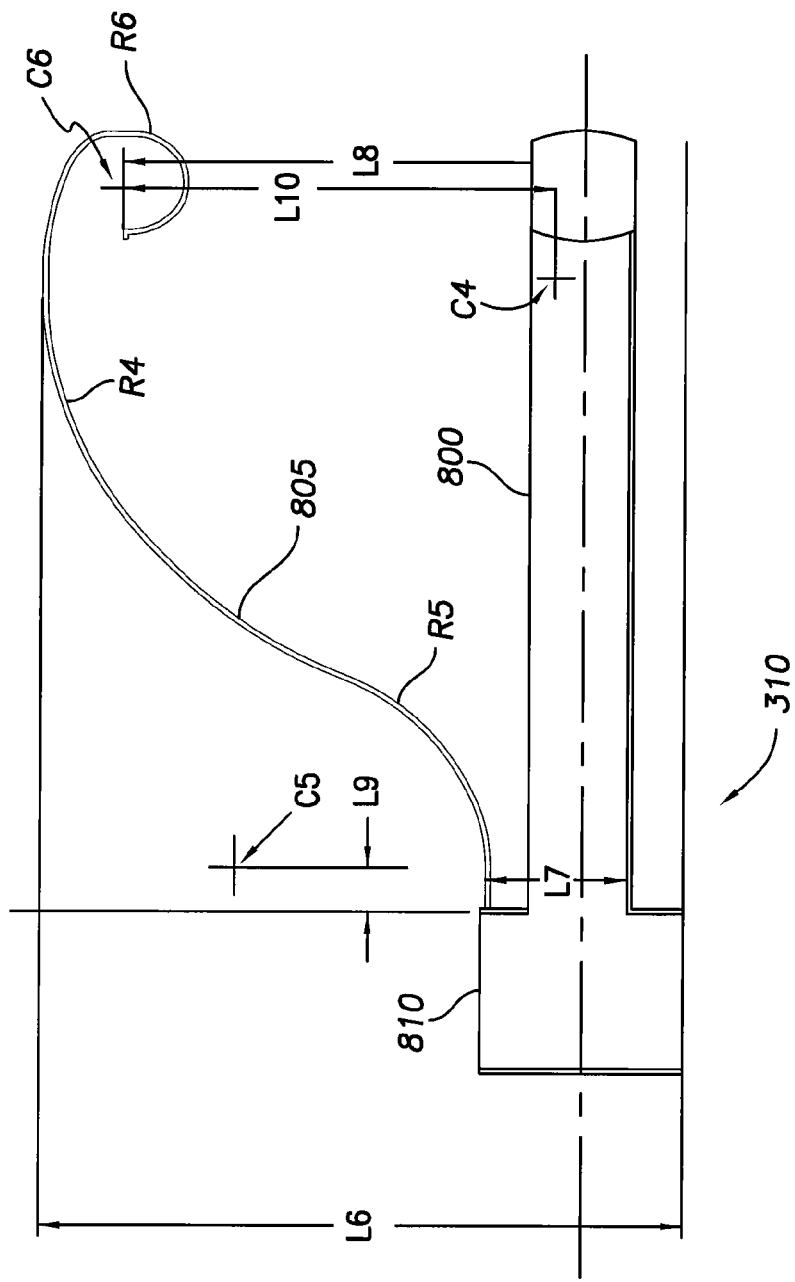
FIG. 19 is an enlarged side view of the fixation member of FIG. 16.
Figure 20:
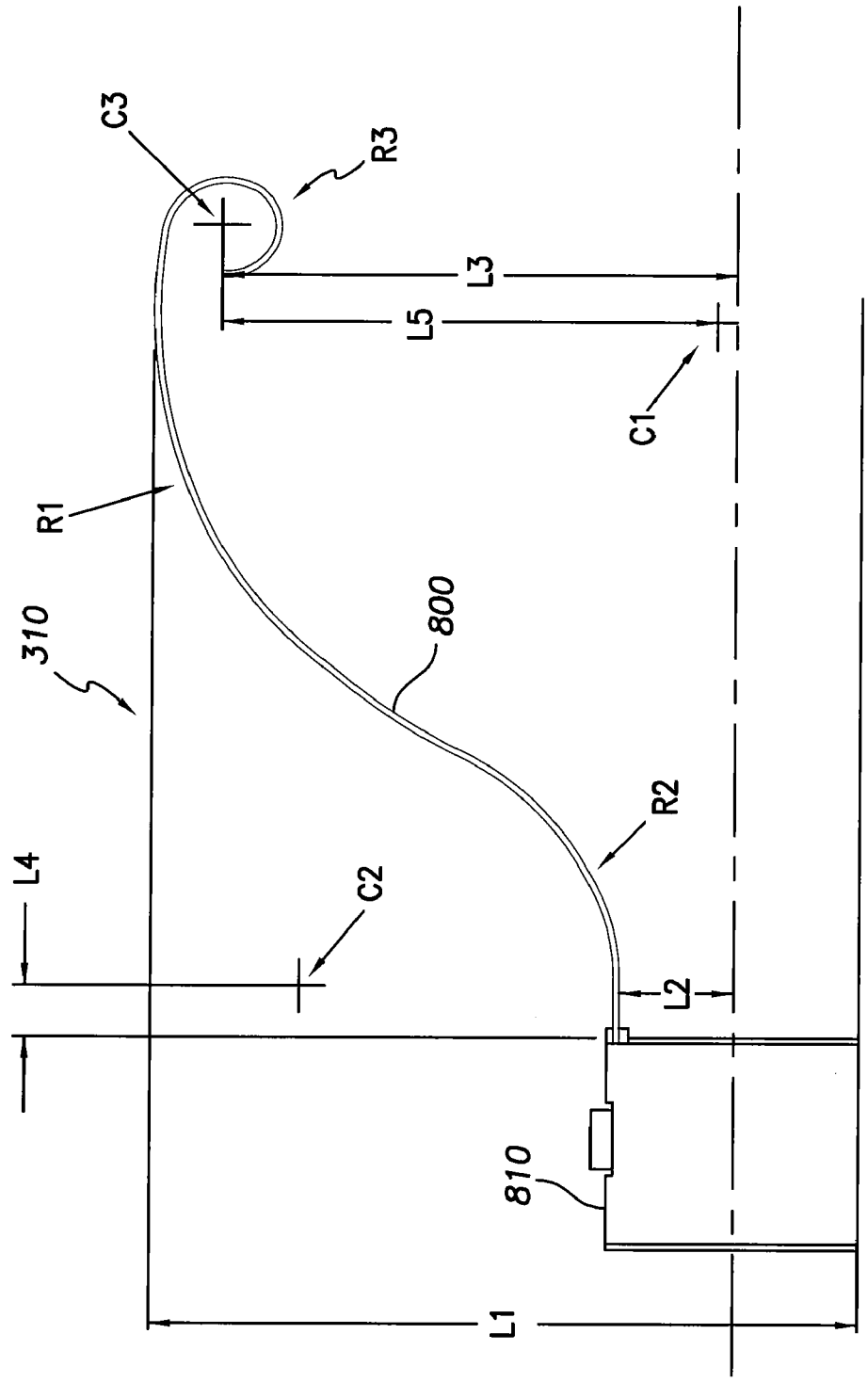
FIG. 20 is an enlarged partial top view of the fixation member of FIG. 16.

As indicated in FIGS. 18 and 19, in one embodiment, the fixation member 310 may be configured as follows. The extreme outer surface of a side tine 800 extends from the far side of the ring portion 810 of the member 310 a distance L1 of approximately 0.22 inch. The side tine 800 extends from the ring portion 810 along a line generally parallel to the centerline of the ring portion 810 and offset from the centerline by a distance L2 of approximately 0.036 inch. The side tine 800 then transitions into a curve with a radius R2 of 0.1 inch, the radius R2 being centered at C2. The side tine 800 then transitions into an opposite curve with a radius R1 of approximately 0.176 inch, the radius R1 being centered at C1. The side tine 800 then transitions into a rolled tip with a radius R3 of 0.017 inch, the radius R3 being centered at C3. The center C2 is proximally offset from a proximal edge of the ring 810 by a distance L4 of approximately 0.02 inch. The center C3 is laterally offset from the centerline of the ring 810 by a distance L3 of approximately 0.16. The center C1 is laterally offset from the center C3 by a distance L5 of approximately 0.1 inch.

With reference to FIG. 18, the extreme outer surface of a top tine 805 extends from the far side of the ring portion 810 of the member 310 a distance L6 of approximately 0.246 inch to approximately 0.25 inch, which is also the distance from the extreme outer surface of the top tine 805 to the epicardium 44, as can be understood from FIG. 11. The top tine 805 extends from the ring portion 810 along a line generally parallel to the centerline of the ring portion 810 and is offset from the centerline by a distance L7 of approximately 0.036 inch. The top tine 805 then transitions into a curve with a radius R5 of 0.1 inch, the radius R5 being centered at C5. The top tine 805 then transitions into an opposite curve with a radius R4 of approximately 0.2 inch, the radius R4 being centered at C4. The top tine 805 then transitions into a rolled tip with a radius R6 of 0.024 inch, the radius R6 being centered at C6. The center C5 is proximally offset from a proximal edge of the ring 810 by a distance L9 of approximately 0.02 inch. The center C6 is laterally offset from the centerline of the ring 810 by a distance L8 of approximately 0.18. The center C4 is laterally offset from the center C6 by a distance L10 of approximately 0.12 inch.

While the embodiments depicted in FIGS. 16-20 and the preceding discussion describe specific dimensional configurations of specific embodiments, in other embodiments the fixation members may have other dimensional configurations. Accordingly, the fixation members disclosed herein should not be considered to being limited to only the above provided dimensions.

In one embodiment, the fixation members 310 are formed of Nitinol or another superelastic material. In one embodiment, the Nitinol or other superelastic material is coated with a polymer such as polytetrafluoroethylene ("PTFE"), parylene, polyurethane, etc. to increase corrosion resistance, cover/reduce sharp edges, and/or reduce frictional resistance.

In one embodiment, any one or more of the fixation members 310 or at least the tines or fingers 320, 800, 805 thereon are formed of biodegradable or bioabsorbable polymers such as polycaprolactone, those that are collagen based, and those belonging to the families of polylactic acid ("PLA") and polyglycolic acid ("PGA").

Candidate materials for making the biodegradable or bioabsorbable portions of the fixation members may include: polycaprolactone; poly(D,L-lactide) poly(L-lactide); polyglycolide; poly(dioxanone); poly(glycolide-co-trimethylene carbonate); poly(L-lactide-co-glycolide); poly(D,L-lactide-co-glycolide); poly(L-lactide-co-D,L-lactide); poly(glycolide-co-trimethylene carbonate-co-dioxanone); poly(D,L lactide-co-glycolide); and etc. In this list of candidate materials, "L" pertains to levorotary and "D" to dextrorotary. The ratios of these isomers of PLA and PGA determine biodegradability over time as well as the stiffness of the resulting component.

In one embodiment, the candidate material is a mixture of PLA/PGA/polycaprolactone, and the ratio of the two isomers can be varied, as is the case with the rest of the aforementioned candidate materials, in order to vary the biodegradability of the candidate material. In one embodiment, the candidate material is a 50/50 mixture of poly(D,L lactide-co-glycolide).

In one embodiment, the candidate material is overmolded onto a substrate (e.g., the lead body where the entire fixation member is formed of the biodegradable material, or ring or base of the fixation member where only the tines are formed of biodegradable material). In other embodiments, the candidate materials are injection molded into appropriate shapes, which are bonded via an adhesive or other methods to the substrate.

The bioabsorbable material degrades or otherwise breaks down over a period of time within the patient and is absorbed. In one embodiment, the bioabsorbable fixation members 310 exist sufficiently long to assist in establishing chronic fixation of the lead 58 within the patient. However, after a sufficient amount of time has passed to allow for chronic fixation of the lead, the bioabsorbable members 310 or the tines 320 thereon will degrade and be absorbed. The resulting absence of the member 310 or tines 320 eases extraction of the lead 58 should the need for lead extraction arise.

In one embodiment, the bioabsorbable material will begin degrading after a period within the patient of between approximately four weeks to approximately six weeks. The bioabsorbable material will be generally completely degraded (at least for purposes of extracting the lead) over a period of approximately six weeks to approximately fifteen weeks within the patient.

As shown in FIG. 5A, an electrical connector assembly 90 carried by the proximal portion 59P of the lead body includes a pin contact 91, a ring contact 92 and annular seals 93. The connector assembly is configured for insertion into a receptacle in a pacemaker or implantable cardio-defibrillator ("ICD") 98 (as indicated by insertion arrow 99). As indicated in FIG. 5A at arrows 94 and 94', which indicate enlarged sectional views of alternative configurations of the lead body 59, electrical conductors in the lumens 95 connect the two electrodes 80 with the pin and ring contacts 91 and 92.

The lumen 96, which is depicted in cross sections 94 and 94' in FIG. 5A, is configured to slidably receive a stylet (100 in FIG. 5B). To enhance the reception of the stylet, the lumen 96 may be lined with a sleeve 97 formed of a low-friction polymer (e.g., PTFE) or a helically wound conductor coil 97, which itself may be coated or lined with a low-friction polymer. In the case of a lumen 96 lined with a coil 97, the coil reinforces the lumen 96 to prevent the stylet 100 from piercing through the lumen 96.

In FIGS. 5A-5D, the distal end portion of the lead body carries two electrodes 80 for bipolar pacing/sensing. In another lead embodiment, the distal end portion of the lead body may carry only one electrode for unipolar pacing and/or sensing, as is well known in the art. In yet other embodiments, the distal end of the lead body may carry three, four or more electrodes for pacing/sensing.

As shown in FIG. 5A, in various embodiments, the lead body 59 includes a shock coil 330 (not shown to scale in FIG. 5A). The shock coil 330 can be located at a variety of locations on the lead body proximal of the electrodes 80 and can be of a variety of lengths. The lead can be coupled to an ICD 98 and the shock coil can be used to deliver high voltage shocks to the heart tissue in response to a tachycardia or fibrillation.

In one embodiment, the loop member 60 can serve in place of, or in addition to, the shock coil 330. In such an embodiment, the one of the electrical conductors 95 is coupled to the loop member 60.

In an exemplary application of the cardiac lead 58 of FIGS. 5A-5D, the stylet 100 is inserted (see FIG. 5B) through the lumen 96 until it abuts the end tip 71. Pressure on the stylet then urges the distal end portion 59D of the lead body 59 and associated loop member 60 into the extended narrowed configuration 70L as shown in FIG. 5B to facilitate implantation via the introducer 55 of FIG. 1 in the subxiphoid region 26. The lead body 59 and loop 60 in the extended narrowed configurations 70L, 60E are fed through the introducer 55 and guided along the insertion path 49 of FIG. 3 into the pericardial space 45 (similar insertion processes are recited in the flow chart 50 of FIG. 4). In this state, the lead body and loop member define a first, thin lead profile.

Once the distal end portion of the lead body and loop are properly inserted into a desired location within the pericardial space, the stylet 100 is withdrawn which permits the lead body and loop to recover to the respective sinuous and expanded diamond configurations. FIG. 6 is a view similar to FIG. 3 (with like elements indicated by like reference numbers), which shows the distal end portion 59D of the lead body in position in the pericardial space 45. Within the pericardial space lays the tip end 71 of the distal end portion 70 and the shield 81, which surrounds the distal end portion and an electrode (70 and 80 in FIG. 5C). The humps 66 of the loop member (60 in FIG. 5C) abut the curved surface of the perietal layer 43, which urges the electrodes towards the epicardium 44. In this state, the lead body and the loop member define a second profile that is wider than the first lead profile Essentially the humps 66 form pressure points that urge the electrodes 80 and prongs 116 carries thereby, into engagement with the epicardium. Although the humps 66 enhance this urging action, other useful embodiments of the cardiac lead 58 can be formed with planar or non-hump versions of the loop 60, as shown by the broken lines in FIG. 5A. The two-dimensional profile of these planar embodiments will also be urged inward by the curved parietal layer 43.

A posterior view of the heart 30 of FIG. 2 is shown in FIG. 7 where heart structures such as the inferior vena cava 90, pulmonary veins 91, pulmonary artery 34, and aortic arch 35 are visible. In FIG. 7, it is assumed that the cardiac lead 58 of FIGS. 5A-5D has been inserted into the pericardial space as shown in FIG. 6. It is further assumed that the lead has been installed on the posterior surface overlying the left ventricle of the heart 30 of FIG. 6.

The sinuous shape of the sinuous configuration 70S of the distal end portion 70 provides verification that the lead 58 has been properly installed and that the electrodes will thereby be urged into the epicardium (44 in FIG. 3) as desired. More specifically, when the lead 58 is viewed fluoroscopically, the observed sinuous shape of the configuration 70S immediately indicates the orientation of the lead and its electrodes. It can be visually confirmed, therefore, that the electrodes are directed towards the epicardium. If the lead 58 is viewed on edge in a lateral view, the offset electrodes (80 in FIG. 5D) will be visible and this will indicate that they are directed into the epicardium.

In another feature of the lead structure, the sinuous configuration 70S provides resilience between the ends 71 and 73 of the distal end portion 70. This resilience allows the electrodes 80 to move (i.e., float) within the loop and track the movement of the epicardium as the heart beats. Contact between the electrodes and the epicardium is thus enhanced during heartbeats. By structuring the distal end portion 70 to be less stiff than the loop member 60, the effectiveness of this feature may be further enhanced.

From the figures and the preceding discussion, it is apparent that different loop embodiments may be structured with different aspect ratios (i.e., ratios of length to width). For example, the aspect ratio shown in FIGS. 5A and 5C is approximately 1 to 1, which is a uniform square shape that will not have a tendency to favor one direction of heart movement over another.

The loop member 60 is formed from various resilient materials. An exemplary material is Nitinol, which is a nickel-titanium alloy. Nitinol has a thermal memory enhances its recovery to its sinuous configuration (70S in FIG. 5A) as it responds to body temperature. Although a medical-grade adhesive 72 may be used to join the distal segment 61 of the loop member to the end 71 of the lead body's distal end portion, other joinder techniques may be used, for example, extrusion, overmolding, reflow (e.g., heat the polymer and let it flow over the section to be joined and then let it harden), etc.

In one embodiment, the loop member 60 has a hemo-compatible and/or lubricious coating. For example, the coating could include an anti-inflammatory and/or an anti-coagulant. Also, the coating could include or be a coating of PTFE, silicone rubber, or polyurethane for minimizing adverse interaction with the tissue lining the pericardial sac, which might lead to thrombosis.

The three dimensional deviation of the lead end portion 70 and loop member 60 as depicted in FIG. 5A is advantageous in that three dimensional deviation promotes a particular orientation of the lead distal end relative to the epicardium and causes the lead 58 to act against the pericardial sac to force the lead distal portion against the epicardium, providing improved electrode contact with the epicardium and improved chronic stability.

With reference again to FIGS. 5A-5E, by way of non-limiting example, the dimensions and other features of various elements of the lead may be as follows:

(1) The diameter of the lead body 59 may be 5½ French.
(2) The loop member 60, deployed as seen in FIGS. 5A and 5C, may have a generally diamond configuration in plan view, measuring, for example, 6½ cm long and 4½ cm wide. It will be apparent that the loop member may have different aspect ratios (i.e., ratios of length to width). For example, an aspect ratio of approximately 1 to 1 (a generally square shape) will not have a tendency to favor one direction of heart movement over another.

(3) The overall length of the loop member 60 in its elongated, contracted configuration (FIG. 5B) may be 8 cm with a contracted width of 12 French so as to be compatible with an introducer having an internal diameter of, for example, 14 French.

(4) The overall diameter of each of the electrodes 80 may be about 1.6-2.0 mm. The prongs 116 may be arranged in a generally circular array (FIGS. 5C and 5E) having a diameter of about 1.9 mm.

(5) The shields 112 and meshes 83 are flexible so that they will contract as they are passed through an introducer. The shields 112 and meshes 83 may have the same diameter of approximately 1 cm; as best seen in FIG. 5E, the shields and meshes are preferably somewhat elliptical in plan view with the longer axis extending longitudinally to facilitate the passage of the electrode assemblies 81 through an introducer and into the pericardial space 45.

Figure 12:
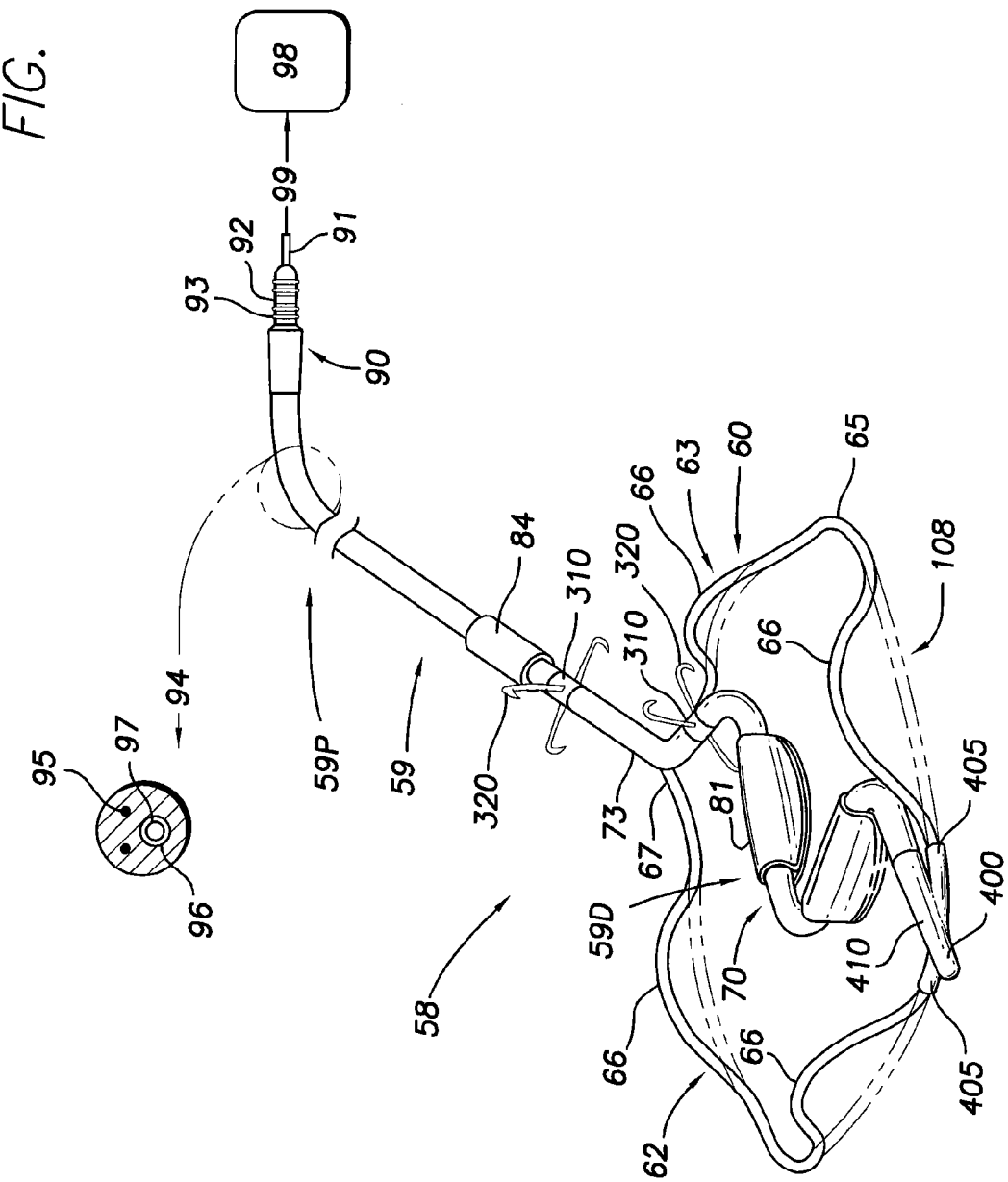
FIG. 12 is the same view depicted in FIG. 5A, except the lead distal end employs a biodegradable or absorbable nosepiece to form a closed arrangement with the lead-body distal end or tip to the arm-member distal ends.
Figure 14:
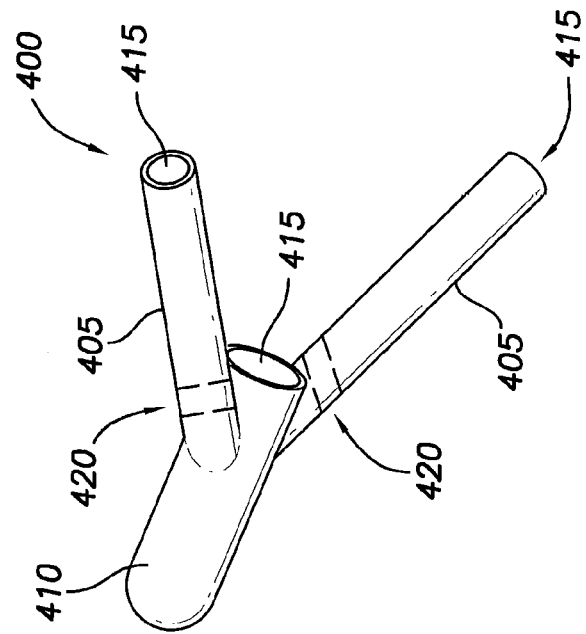
FIG. 14 is an isometric view of the biodegradable nosepiece employed in FIG. 12.
Figure 13:
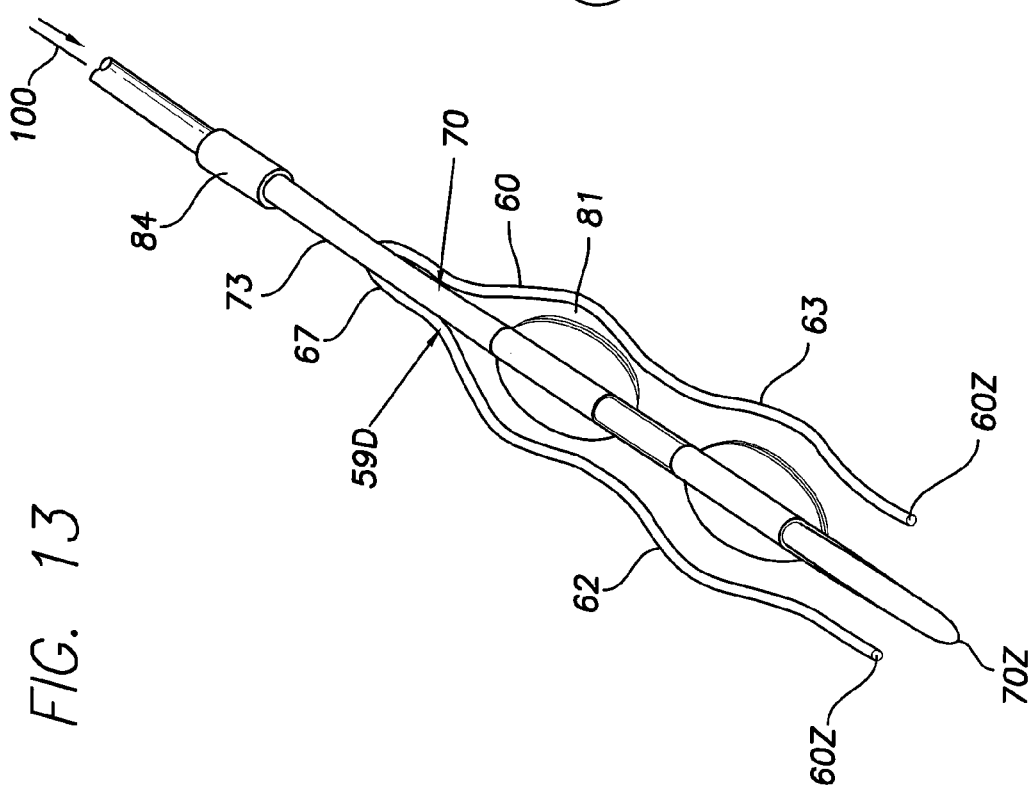
FIG. 13 is the same view depicted in FIG. 5B, except the nosepiece has degraded/dissolved within the body and has been absorbed, thereby freeing the arm-member distal ends from each other and from the body distal tip to provide an open arrangement.
Figure 15:
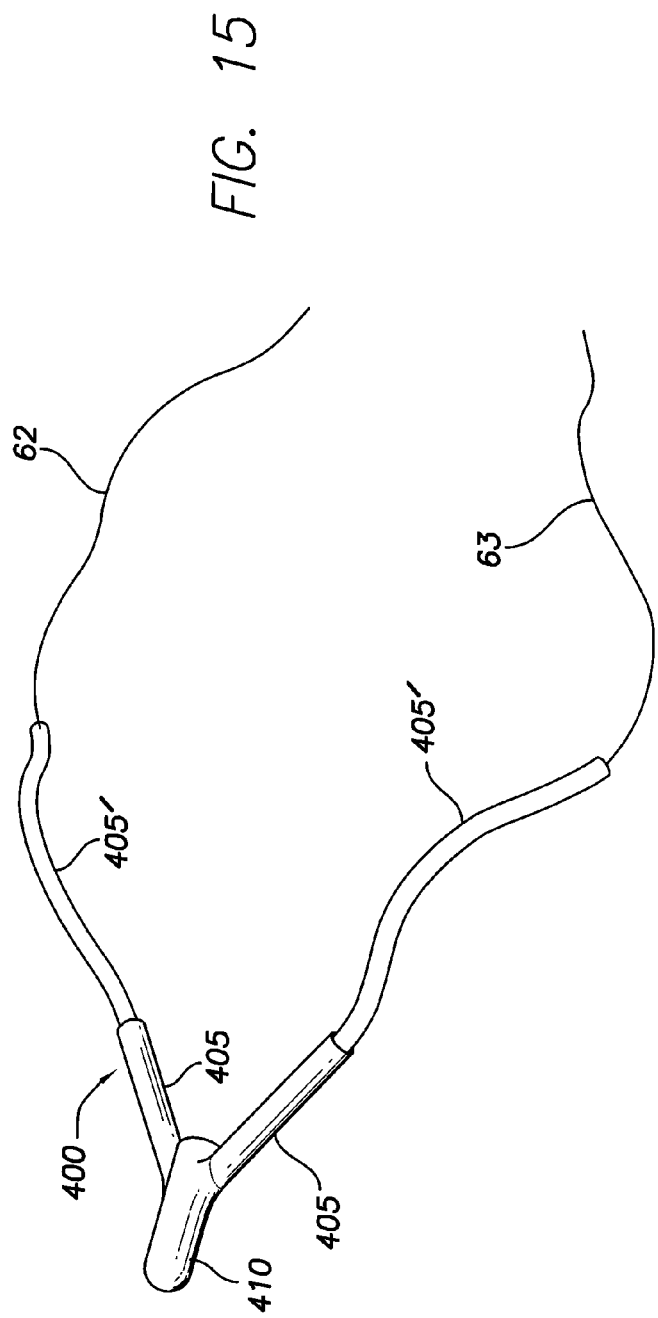
FIG. 15 is an isometric view of the nosepiece of FIG. 14, except the side legs are extended or have extensions.

For a discussion regarding an embodiment of the lead 58 having an alternative distal end configuration, reference is made to FIGS. 12-15. FIG. 12 is the same view depicted in FIG. 5A, except the lead distal end employs a biodegradable or absorbable nosepiece 400 to couple the lead body 59 distal end or tip 70Z and one or more of the loop portion or arm member 62, 63 distal ends 60Z together such that the nosepiece 400, and distal regions of the arm members 62, 63 and lead body 59 interconnect to form a closed arrangement. FIG. 13 is the same view depicted in FIG. 5B, except the nosepiece 400 has degraded/dissolved within the body and has been absorbed, thereby decoupling the arm-member distal ends 60Z and the lead-body distal tip 70Z, such that the distal regions of the arm members 62, 63 and lead body 59 form an open arrangement. FIG. 14 is an isometric view of the biodegradable nosepiece 400 employed in FIG. 12. FIG. 15 is an isometric view of the nosepiece 400 of FIG. 14, except the side legs 405 are extended or have extensions 405'.

As shown in FIG. 14, in one embodiment, the nosepiece 400 includes a tubular center leg 410 and tubular side legs 405 obliquely intersecting the center leg 410. The legs 405, 410 include openings 415, which, as can be understood in FIG. 12, receive the lead-body distal tip (70Z in FIG. 13) and the arm-member distal ends (60Z in FIG. 13). The nosepiece 400 serves as a coupling device that essentially "joins" the distal ends 70Z, 60Z so that they function as interconnected elements, without being physically and fixedly joined together. In other words, the distal ends 60Z, 70Z are not permanently joined together, for example by adhesive, but instead are placed in an adjacent, and perhaps non-contacting, arrangement, through the nosepiece, to thereby form—in conjunction with the nosepiece—a closed arrangement or loop at the distal region of the lead.

As indicated in FIG. 15, in one embodiment, one or more of the side legs 405 are substantially elongated or coupled to extensions 405' that extend the side legs 405 a substantial distance. For example, in one embodiment, the side legs 405 or side leg extensions 405' are between approximately 1.5 to approximately five times the length of the center leg 410. In one embodiment, the entire nosepiece 400 and extensions 405', if present, are both biodegradable. In another embodiment, the entire nosepiece 400 is biodegradable and the extensions 405' are not biodegradable.

As indicated in FIG. 14, in one embodiment, segments 420 of the nosepiece 400 are biodegradable while the rest of the nosepiece 400 is not biodegradable. The segments 420 are positioned such that when the lead body 59 and arm members 62, 63 are received by the nosepiece, the segments are between the distal ends and tips of these elements. The segments 420 dissolve, severing the side legs 405 from the center leg 410, thereby freeing the distal ends 70Z, 60Z from their coupled arrangement and allowing them to transition into an open arrangement, as shown in FIG. 13.

In one embodiment, the nosepiece 400 is formed of biodegradable or bioabsorbable polymers such as polycaprolactone, biodegradable or boiabsorbable polymers that are collagen based, and/or biodegradable or bioabsorbable polymers that belong to the families of polylactic acid ("PLA") and/or polyglycolic acid ("PGA").

Candidate materials for making the biodegradable or bioabsorbable portions of the fixation members may include: polycaprolactone; poly(D,L-lactide) poly(L-lactide); polyglycolide; poly(dioxanone); poly(glycolide-co-trimethylene carbonate); poly(L-lactide-co-glycolide); poly(D,L-lactide-co-glycolide); poly(L-lactide-co-D,L-lactide); poly(glycolide-co-trimethylene carbonate-co-dioxanone); poly(D,L lactide-co-glycolide); and etc. In this list of candidate materials, "L" pertains to levorotary and "D" to dextrorotary. The ratios of these isomers of PLA and PGA determine biodegradability over time as well as the stiffness of the resulting component.

In one embodiment, the candidate material is a mixture of PLA/PGA/polycaprolactone, and the ratio of the two isomers can be varied, as is the case with the rest of the aforementioned candidate materials, in order to vary the biodegradability of the candidate material. In one embodiment, the candidate material is a 50/50 mixture of poly(D,L lactide-co-glycolide).

In one embodiment, the candidate material is overmolded onto a substrate (e.g., the lead body). In other embodiments, the candidate materials are injection molded into appropriate shapes, which are bonded via an adhesive or other methods to the substrate.

The bioabsorbable material degrades or otherwise breaks down over a period of time within the patient and is absorbed. In one embodiment, the bioabsorbable nosepiece 400 exists as a support for the loop 60 to allow the loop 60 to assist in maintaining the diamond-shaped configuration (shown in FIG. 12) sufficiently long to establish chronic fixation of the lead 58 within the patient through, for example, tissue ingrowth in the mesh sections of the electrode assemblies 81. However, after a sufficient amount of time has passed to allow for chronic fixation of the lead, the nosepiece 400 degrades and is absorbed. During this time, however, tissue may grow in the region of the nosepiece and may, for example, grow over and on both sides (i.e., within the loop and outside the loop) of the closed arrangement of the loop arm members 62, 63 and lead body 59.

As can be understood from FIG. 13, in the absence of the nosepiece 400, the loop arm members 62, 63 and lead body 59 decouple and thereby transition from the looped, intersected or closed-end formed by the intersection of the distal ends 70Z, 60Z, as shown in FIG. 12, to the open arrangement shown in FIG. 13. Due to the removal of the intersecting arrangement of the ends 70Z, 60Z, the lead body 59 and the arms 62, 63 can be withdrawn from tissue overgrowth present in the region where the nosepiece was. Such extraction would otherwise be impeded were the closed arrangement of the ends 70Z, 60Z still present. Thus, extraction of the lead 58 is substantially eased, should the need for lead extraction arise In one embodiment, the bioabsorbable material begins degrading after a period within the patient of between approximately four weeks to approximately six weeks. The bioabsorbable material is generally completely degraded (at least for purposes of extracting the lead) over a period of approximately six weeks to approximately fifteen weeks within the patient.

As indicated in FIG. 12, in one embodiment, the lead includes both a biodegradable nosepiece 400 and one or more biodegradable fixation members 310 or fixation members 310 having biodegradable tines 320. In one embodiment, the nosepiece 400 and the members 310 or tines 320 degrade at relatively the same rate an over same period. As a result, the nosepiece 400 and members (or tines of the members as the case may be) cease to exist at generally the same period in time.

In other embodiments, the biodegradable nosepiece 400 and fixation members 310 or tines 320 degrade at different rates and over different time periods. For example, in one such embodiment, the tines or fixation members cease to exist before the nosepiece ceases to exist. In another embodiment, the opposite is true, with the nosepiece ceasing to exist first and the fixation members or tines second.

The embodiments of the invention described herein are exemplary and numerous modifications, variations and rearrangements can be readily envisioned to achieve substantially equivalent results, all of which are intended to be embraced within the spirit and scope of the appended claims.

What is claimed is:

1. An intrapericardial lead for delivery via a percutaneous puncture and configurable by insertion of a stylet into the lead, the lead comprising:
    a lead body including a stylet receiving lumen, a distal tip, and a distal portion proximal of the distal tip and biased to assume a non-linear configuration, wherein insertion of the stylet into the lumen such that the distal tip is distally displaced relative to the rest of the lead body causes the distal portion to transition from the non-linear configuration to a generally linear configuration;
    a first arm member having a distal end, and a proximal end coupled to the lead body proximal of the distal tip; and
    a nosepiece, at least a portion of which is biodegradable, having a first leg defining a first lumen opening configured to receive the distal tip of the lead body and a second leg defining a second lumen opening configured to receive the distal end of the first arm member, wherein the first leg and the second leg obliquely intersect such that the lead body, first arm member and nosepiece form a closed arrangement prior to biodegradation of the nosepiece and an open arrangement after biodegradation of the nosepiece, wherein in the closed arrangement the lead body and the first arm have non-uniform spacing there between along their respective lengths, and wherein the biodegradable portion of the nosepiece is configured to degrade to allow for the open arrangement after a time sufficient to allow for chronic fixation of the lead.

2. The lead of claim 1, wherein at least a portion of the nosepiece is formed of a biodegradable or bioabsorbable polymer.

3. The lead of claim 2, wherein the polymer includes collagen based polymer.

4. The lead of claim 2, wherein the polymer includes a polymer belonging to at least one of the families of polylactic acid ("PLA") and polyglycolic acid ("PGA").

5. The lead of claim 2, wherein the polymer includes polycaprolactone.

6. The lead of claim 1 wherein the entire nosepiece is biodegradable.

7. The lead of claim 1 wherein the nosepiece comprises a biodegradable segment between the distal tip of the lead body and the distal end of the first arm member.

8. The lead of claim 1, further comprising a second arm member having a distal end, and a proximal end coupled to the lead body proximal of the distal tip, wherein the nosepiece is further includes a third leg defining a third lumen opening configured to receive the distal end of the second arm member such that the lead body, first arm member, second arm member and nosepiece form a closed arrangement prior to biodegradation of the nosepiece and an open arrangement after biodegradation of the nosepiece.

9. The lead of claim 8, wherein the first leg and the third leg obliquely intersect.

10. The lead of claim 8, wherein the second and third legs extend along the arm members a distance of between approximately 1.5 to approximately five times the length of the first leg.

11. The lead of claim 1 wherein the biodegradable portion of the nosepiece is configured to begin degrading after a period within a patient of between approximately four weeks to approximately six weeks.

12. The lead of claim 1 wherein the biodegradable portion of the nosepiece is configured to be completely degraded over a period within a patient of between approximately six weeks to approximately fifteen weeks.

13. The lead of claim 1 wherein the first leg is formed of a non-biodegradable material and the second leg is formed at least partially of a biodegradable or bioabsorbable polymer.

14. The lead of claim 13 wherein the second leg comprises a portion that is formed of a non-biodegradable material.

15. A lead comprising:
a lead body including a distal tip, and a distal portion proximal of the distal tip;
a first arm member having a distal end, and a proximal end coupled to the lead body proximal of the distal tip; and
a nosepiece, at least a portion of which is biodegradable, having a first leg defining first lumen opening configured to receive the distal tip of the lead body and a second leg defining a second lumen opening configured to receive the distal end of the first arm member, wherein the first leg and the second leg obliquely intersect such that the lead body, first arm member and nosepiece form a closed arrangement prior to biodegradation of the nosepiece and an open arrangement after biodegradation of the nosepiece, wherein in the closed arrangement the lead body and the first arm have non-uniform spacing there between along their respective lengths, and wherein the biodegradable portion of the nosepiece is configured to degrade to allow for the open arrangement after a time sufficient to allow for chronic fixation of the lead.

16. The lead of claim 15 further comprising a fixation member mounted on the lead body and including a biodegradable portion.

17. The lead of claim 16, wherein the fixation member includes an element radially projecting outward from the lead body.

18. The lead of claim 17, wherein the element also projects distally.

19. The lead of claim 17, wherein the element is biased to expand away from the lead body.

20. The lead of claim 17, wherein the element comprises the biodegradable portion.

21. The lead of claim 16, wherein the biodegradable portion is a biodegradable or bioabsorbable polymer.

22. The lead of claim 21, wherein the polymer includes collagen based polymer.

* * * * *